(12) United States Patent
Kiilerich et al.

(10) Patent No.: US 11,197,957 B2
(45) Date of Patent: Dec. 14, 2021

(54) DRUG DELIVERY DEVICE WITH END-OF-DOSE TRIGGER ARRANGEMENT

(71) Applicant: Novo Nordisk A/S, Bagsvaerd (DK)

(72) Inventors: Ebbe Kiilerich, Copenhagen NV (DK); Jesper Peter Windum, Hilleroed (DK); Christian Plambech, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 406 days.

(21) Appl. No.: 15/738,393

(22) PCT Filed: Jul. 5, 2016

(86) PCT No.: PCT/EP2016/065807
§ 371 (c)(1),
(2) Date: Dec. 20, 2017

(87) PCT Pub. No.: WO2017/009102
PCT Pub. Date: Jan. 19, 2017

(65) Prior Publication Data
US 2018/0161503 A1     Jun. 14, 2018

(30) Foreign Application Priority Data
Jul. 13, 2015    (EP) .................................... 15176383

(51) Int. Cl.
*A61M 5/20* (2006.01)
*A61M 5/24* (2006.01)
(Continued)

(52) U.S. Cl.
CPC ................ *A61M 5/20* (2013.01); *A61M 5/24* (2013.01); *A61M 5/3157* (2013.01);
(Continued)

(58) Field of Classification Search
CPC ...... A61M 5/20; A61M 5/24; A61M 5/31525; A61M 5/3157; A61M 5/31585;
(Continued)

(56) References Cited

U.S. PATENT DOCUMENTS

| | | |
|---|---|---|
| 7,008,399 B2 | 3/2006 | Larsen et al. |
| 2002/0188419 A1 | 12/2002 | Slate et al. |

(Continued)

FOREIGN PATENT DOCUMENTS

| | | |
|---|---|---|
| CN | 104321096 | 1/2015 |
| JP | H11267206 A | 10/1999 |

(Continued)

*Primary Examiner* — Lauren P Farrar
(74) *Attorney, Agent, or Firm* — Wesley Nicolas

(57) ABSTRACT

A drug delivery device comprising a rotatable scale drum, a trigger member, an actuation member, a trigger spring acting on the trigger member and being energized by movement of the actuation member, as well as an end-of-dose switch adapted to be actuated by movement of the trigger member. The trigger member is adapted to be arranged in an axially supported position against the action of the energized trigger spring, and released from the axially supported position when the scale drum is rotated from a set position to an end-of-dose position, whereby the trigger member is moved axially by the trigger spring, the end-of-dose switch thereby being actuated.

14 Claims, 11 Drawing Sheets

(51) Int. Cl.
*A61M 5/315* (2006.01)
*A61M 5/31* (2006.01)

(52) U.S. Cl.
CPC .... *A61M 5/31525* (2013.01); *A61M 5/31585* (2013.01); *A61M 5/31551* (2013.01); *A61M 5/31553* (2013.01); *A61M 5/31593* (2013.01); *A61M 2005/202* (2013.01); *A61M 2005/2403* (2013.01); *A61M 2005/2407* (2013.01); *A61M 2005/2411* (2013.01); *A61M 2005/3126* (2013.01); *A61M 2205/52* (2013.01)

(58) Field of Classification Search
CPC ...... A61M 2005/2411; A61M 5/31553; A61M 2005/2407; A61M 2005/2403; A61M 5/31551; A61M 5/31593; A61M 2005/202; A61M 2005/3126; A61M 2205/52
See application file for complete search history.

(56) References Cited

U.S. PATENT DOCUMENTS

2009/0318865 A1* 12/2009 Moller .............. A61M 5/31583
604/135
2012/0053527 A1  3/2012 Cirillo et al.
2016/0287808 A1* 10/2016 Madsen .............. G06F 19/3456

FOREIGN PATENT DOCUMENTS

| | | |
|---|---|---|
| JP | 2014517734 A | 7/2014 |
| JP | 2014525326 A | 9/2014 |
| JP | 2014530691 A | 11/2014 |
| WO | 2010052275 A2 | 5/2010 |
| WO | 2010098927 A1 | 9/2010 |
| WO | 2012140097 | 10/2012 |
| WO | 2013057034 | 4/2013 |
| WO | 2013/098421 A1 | 7/2013 |
| WO | 2013120778 A1 | 8/2013 |
| WO | 2013144023 | 10/2013 |
| WO | 2014/020008 A1 | 2/2014 |
| WO | 2014180745 A1 | 11/2014 |
| WO | 2015/071354 A1 | 5/2015 |
| WO | 2015084428 | 6/2015 |

\* cited by examiner

DRUG DELIVERY DEVICE WITH END-OF-DOSE TRIGGER ARRANGEMENT

CROSS-REFERENCE TO RELATED APPLICATIONS

This application is a 35 U.S.C. § 371 National Stage application of International Application PCT/EP2016/065807 (published as WO 2017/009102), filed Jul. 5, 2016, which claims priority to European Patent Application 15176383.6, filed Jul. 13, 2015, the contents thereof which are incorporated by reference in their entirety.

The present invention relates to devices, assemblies and systems adapted for capturing information. In a specific aspect the invention addresses issues relating to electronic dose data capturing in and for a drug delivery device.

BACKGROUND OF THE INVENTION

In the disclosure of the present invention reference is mostly made to the treatment of diabetes by delivery of insulin using a drug delivery device, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Correspondingly, a number of injection devices with a dose monitoring/acquisition feature have been provided, see e.g. US 2009/0318865, WO 2010/052275 and U.S. Pat. No. 7,008,399. However, most devices of today are without it.

Having regard to the above, it is an object of the present invention to provide a drug delivery device as well as components and assemblies therefore which cost-effectively and reliably allows detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a general aspect of the invention a drug delivery device is provided, comprising a drug-filled cartridge or means for receiving a drug-filled cartridge, drug expelling means, as well as sensor means. The cartridge comprises an outlet and an axially displaceable piston. The drug expelling means comprises dose setting means allowing a user to set a dose amount of drug to be expelled, a piston rod adapted to engage and axially move the piston to thereby expel an amount of drug from the cartridge through the outlet, and an indicator member adapted to rotate corresponding to a reference axis from an initial end-of-dose position to a set position corresponding to a set dose amount, and to rotate from the set position back to the end-of-dose position when the set dose has been expelled. The expelling means further comprises a trigger member, an actuation member for causing the piston rod to expel the set dose amount, the actuation member being movable between an initial position and an actuated position, and a trigger spring acting on the trigger member, the trigger spring being energized by movement of the actuation member. The sensor system comprises electronic circuitry adapted to generate and store data related to an expelled dose amount, an end-of-dose switch adapted to be actuated, directly or indirectly, by axial movement of the trigger member, and electronic circuitry adapted to detect when the end-of-dose switch is actuated, the detection being indicative of a set dose amount having been expelled. The trigger member is adapted to be arranged in an axially supported biased position against the action of the energized trigger spring, and released from the axially supported biased position by the indicator member, directly or indirectly, when the indicator member is rotated from a set position to the end-of-dose position, whereby the trigger member is moved axially by the trigger spring, the end-of-dose switch thereby being actuated providing an end-of-dose input to the electronic circuitry.

As appears, the trigger member provides that a rotational movement is used to generate an axial movement, the axial movement being driven by a spring energized during actuation of the actuation member. By this arrangement an end-of-dose condition can be detected in a simple, reliable and effective way.

The trigger member may be moved from a first trigger position to a second trigger position, e.g. by rotation, when the indicator member is rotated from the initial end-of-dose position to a set position, and may be moved from the second trigger position back to the first trigger position when the indicator member is rotated from a set position to the end-of-dose position. When the actuation member is actuated with the trigger member in the second trigger position, then the trigger member is moved back to the first trigger position when the indicator member is rotated from a set position to the end-of-dose position, whereby the trigger member is moved axially by the trigger spring.

The trigger member may be rotationally biased from the first trigger position to the second trigger position by a spring force. The rotational spring force may be provided by the trigger spring or by a separate spring element. The trigger spring, the biasing spring or a combined spring may be provided in the form of separate spring members, e.g. metallic or polymeric springs, or may by formed integrally with a given polymeric component.

In a first specific aspect of the invention a drug delivery device is provided wherein, when the trigger member is in the second trigger position, the trigger member is moved axially from an initial position to an actuated position when the actuation member is moved from the initial position to the actuated position, whereby the trigger spring is energized.

In an exemplary embodiment the actuation member is adapted to engage and thereby move the trigger member axially from the initial to the actuated position, and the actuation member and the trigger member comprise cooperating locking means preventing non-axial movement there between when engaged. The locking means may be arranged to be released and the trigger member to be rotated from the second to the first position when the indicator member is rotated from a set position to the end-of-dose position, this allowing the trigger member to move from the actuated position back to the initial position. The device may comprise biasing means for biasing the trigger member towards the second position, e.g. provided by the trigger spring.

In a second specific aspect of the invention a drug delivery device is provided wherein the trigger spring is energized when the actuation member is moved from the actuated position to the initial position with the trigger member in the second trigger position.

In an exemplary embodiment the trigger member is arranged to axially engage a support when the actuation member is moved from the initial position to the actuated position with the trigger member in the second trigger position. The trigger member may be arranged to be released from the support and rotated from the second to the first position when the indicator member is rotated from a set position to the end-of-dose position, this allowing the trigger member to be moved axially by the trigger spring. The device may comprise biasing means for biasing the trigger member towards the second position, e.g. provided by the trigger spring. Alternatively the biasing means may be formed integrally with the trigger member.

Depending on the design of the dose setting and expelling mechanism different structures could be used to provide an axial support structure, e.g. a movable member such as the actuation member, or a stationary structure such as a housing portion.

The end-of-dose switch may be arranged at any desired location in which it can be actuated by the trigger member. For example, it may be coupled to and move axially with the actuation member. The end-of-dose switch may be adapted to be actuated from an open to a closed state or from a closed to an open state.

Depending on the design of the dose setting and expelling mechanism the above-described end-of-dose arrangement may be activated during use states which are not a "true" end-of-dose state. In this context a "true" end-of-dose state could be considered when an end-of-dose state is detected at the end of an expelling event. For example, for a given design, if the actuation member is actuated and then released with the device in its initial state without a dose being set, then the end-of-dose switch may be activated. To deal with this situation a mode switch may be provided which detects that the actuation member is in its actuated position. Correspondingly, the electronic circuitry would be able to disregard an end-of-dose signal if the actuation member is not in its actuated position as detected by the mode switch. Alternatively, a rotary sensor may be used to detect that no dose has been set, this indicating that the dose button has been actuated with the device in its initial state.

The generated and stored data related to an expelled dose amount may be in the form of e.g. time and/or dose size. For example, when an end-of-dose signal is detected a time stamp may be generated and stored. In addition the electronic circuitry may be adapted to determine the size of a set or expelled dose amount, the dose size being stored when an-end-of dose signal is detected.

In the above-described embodiments of a drug delivery device the drug expelling means may comprise a drive spring, the dose setting means being adapted to simultaneously set the dose amount to be expelled and strain the drive spring correspondingly, and the actuation means being adapted to release the drive spring to thereby move the piston rod in the distal direction corresponding to the set dose.

The indicator member may be in the form of a scale drum member provided with a plurality of dose size indices and being adapted to rotate helically corresponding to a general axis from an initial end-of-dose position in which no dose has been set to a set position corresponding to a set dose amount, and to rotate from the set position back to the end-of-dose position when the set dose has been expelled (or the mechanism has been dialed back to zero). Alternatively, the drug delivery device may be provided with sensor and display means allowing the size of a set dose to be detected electronically and displayed on a display to the user. In such a design the indicator member can be incorporated in the dose setting and expelling mechanism without being visible to the user.

The above-described embodiments of a drug delivery device may further comprise first and second rotary sensor parts adapted to rotate relative to each other during dose setting and/or dose expelling, wherein the electronic circuitry is adapted to calculate dose amounts based on relative rotation between the first and second rotary sensor parts during setting and/or expelling of a dose of drug. A dose amount may be calculated when the electronic circuitry receives an input from the end-of-dose switch. The electronic circuitry may be provided with logging means adapted to create a log for calculated dose amounts of drug. The drug delivery device may further comprise a display controlled by the electronic circuitry and adapted to display dose related data, e.g. dose size and the time since last dose. The electronic circuitry may further comprise transmitter means adapted to transmit stored data to an external receiver.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following exemplary embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The terms "assembly" and "subassembly" do not imply that the described components necessarily can be assembled to provide a unitary or functional assembly or subassembly during a given assembly procedure but is merely used to describe components grouped together as being functionally more closely related.

Figure 1:
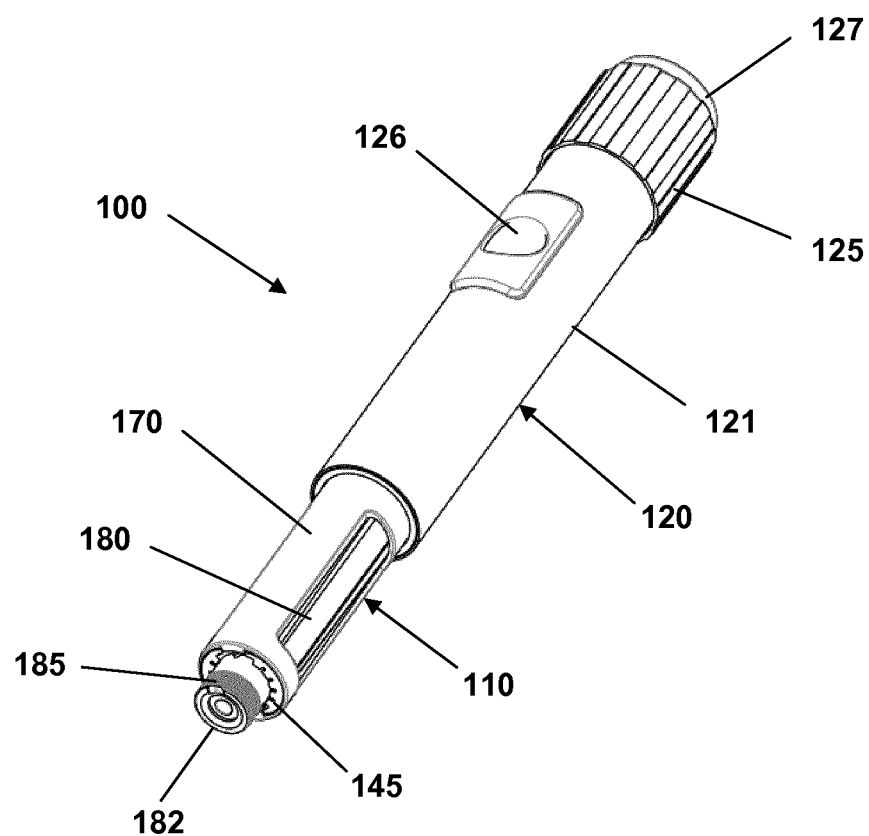
FIGS. 1 and 2 show a front-loaded drug delivery device with respectively without a drug cartridge mounted.

Referring to FIG. 1 a pen-formed drug delivery device 100 will be described. The device represents a "generic" drug delivery device providing an example of a device in combination with which embodiments of the present invention is intended to be used, such a device comprising a rotational member adapted to rotate corresponding to a set and/or expelled dose of drug.

More specifically, the pen device comprises a cap part (not shown) and a main part having a proximal body or drive assembly portion 120 with a housing 121 defining a general axis and in which a drug expelling mechanism is arranged or integrated, and a distal cartridge holder portion in which a drug-filled transparent cartridge 180 with a distal needle-penetrable septum can be arranged and retained in place by a cartridge holder 110 attached to the proximal portion, the cartridge holder having openings allowing a portion of the cartridge to be inspected. The cartridge may for example contain an insulin, GLP-1 or growth hormone formulation. The shown device is of the front-loaded type and is designed to be loaded by the user with a new cartridge through a distal receiving opening in the cartridge holder, the cartridge being provided with a piston driven by a piston rod 128 forming part of the expelling mechanism.

The mechanism comprises a scale drum member provided with a plurality of dose size indices (not shown), the scale drum member being arranged rotationally corresponding to the general axis. The housing comprises a display opening (or window) 126 arranged to show a scale member dose size indicia corresponding to a set dose.

A proximal-most rotatable dose ring member 125 serves to manually set a desired dose of drug shown in display window 126 and which can then be expelled when the release button 127 is actuated. The dose member and release button may be in the form of a combined dose setting and release button. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. In such an embodiment the release button could be considered a "drive button". The cartridge is provided with distal coupling means in the form of a needle hub mount 182 having, in the shown example, an external thread 185 adapted to engage an inner thread of a corresponding hub of a needle assembly. In alternative embodiments the thread may be combined with or replaced by other connection means, e.g. a bayonet coupling.

Figure 2:
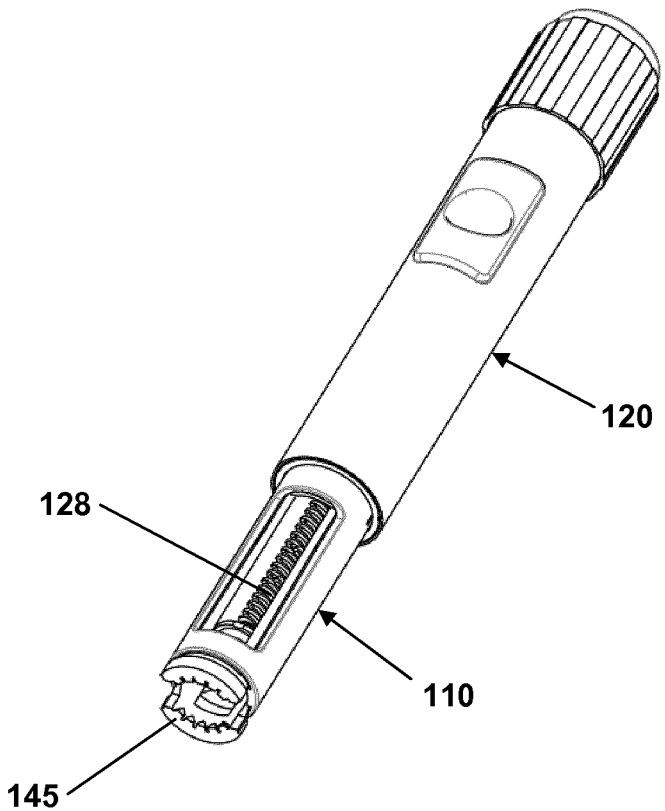

The cartridge holder comprises a distal opening adapted to receive a cartridge. More specifically, the cartridge holder comprises an outer rotatable tube member 170 operated by the user to control movement of gripping means to thereby open and close gripping shoulders 145 configured to grip and hold a cartridge. FIG. 2 shows the device with the cartridge removed and the gripping shoulders in their unlocked "open" position in which a cartridge can be removed and a new inserted.

As appears, FIG. 1 shows a drug delivery device of the front-loaded type in which a cartridge is inserted through a distal opening in the cartridge holder which in non-removable attached to the main part of the device, however, the drug delivery device may alternatively be of the rear-loaded type and comprise a cartridge holder adapted to be removed from the device main portion and in which a cartridge is received and removed through the proximal opening.

The drug delivery device 100 is provided with sensor means and electronic circuitry adapted to create a log for dose amounts of drug expelled from a cartridge by the drug expelling means, wherein the dose amounts are calculated based on relative movement between sensor parts during setting and/or expelling of a dose of drug. The sensor means may be in the form of a rotary sensor adapted to detect rotational movement between two sensor parts, typically a stationary sensor part and a sensor part which rotates during setting and/or expelling of a dose of drug, e.g. as disclosed in WO 2014/128156. In order to safely detect that a given dose has been expelled an EoD sensor (or switch) may be provided adapted to detect when a given dose has been fully expelled. To safely actuate the switch a trigger arrangement may be provided transforming an input movement to an output movement suited for actuation of the EoD switch.

With reference to schematic FIGS. 3A-3E a first embodiment (representing a first concept) of a trigger arrangement 200 for a drug delivery device of the spring-driven type will be described. Each of the figures schematically shows an indicator member in the form of a scale drum member 210, a housing part 220 represented by a number of splines 221, an actuation member in the form of a combined dose setting and release member ("dose button") 230 represented by a number of splines, a trigger member 240, a trigger spring 249, a dose button return spring (not shown), and an End-of-Dose ("EoD") switch 250.

The housing part comprises an axial trigger member stop surface 222 which in the shown embodiment is provided by one or more distally facing surfaces of housing spline elements (in the following also "housing shelf") and a rotational trigger member stop surface 223 (in the following also "housing stop"), an axial button stop surface (not shown), and a trigger spring support 226. The dose button 230 comprises an outer dose dial gripping surface (not shown), a proximal actuation surface (not shown), and a plurality of spline elements 231 each having a distally facing trigger member surface (in the following also "button shelf") which in the shown embodiment is in the form of locking surface 232. The scale drum member 210 comprises a rotational trigger member stop surface 214 (in the following also "drum stop"). The EoD switch 250 is in the shown embodiment attached to the dose button and comprises a stationary portion (relative to the button) 255 and a movable portion in the form of a flexible arm 256, the two portions each comprising a contact point adapted to be arranged in an open respectively closed state. The trigger member 240 comprises a trigger spline 211 adapted to be arranged between housing splines and engage the above-described stop surface 223. In the shown embodiment the trigger member spline has a proximal surface 242 adapted to engage a given dose shelf locking surface 232 and comprises a corresponding locking structure 242 preventing non-axial movement between the two surfaces. The trigger member further comprises a proximal switch surface 246 adapted to axially engage the flexible switch arm 256 to thereby close the switch 250. The trigger spring 249 is arranged between the trigger spring support 226 and the trigger member 240 and serves to provide (i) a radially oriented biasing force to the trigger member (see below) and (ii) a proximally directed biasing force ("trigger force"). The dose button return spring (not shown) is arranged between a support (e.g. the housing) and the dose button 230 and provides a proximally directed return force to the dose button.

The dose button 230 is axially movable between an initial proximal position in which a user can rotate the button (or "dial") to set a dose amount of drug to be expelled, and an actuated distal position in which the expelling mechanism is released when a dose has been set. The scale drum member 210 is adapted to rotate helically corresponding to the general axis from an initial end-of-dose position in which no dose has been set to a set position corresponding to a set dose amount, and to rotate from the set position back to the end-of-dose position when the set dose has been expelled (or the mechanism has been dialed back to zero). The trigger member 240 is adapted to move between (i) a first trigger position in contact with the drum stop 214 when the latter is in the initial end-of-dose position, and (ii) a second trigger position in contact with the housing stop 223. The trigger member 240 is further adapted to move between (i) a first axial position in contact with the housing shelf 222, to (ii) a second axial position in contact with the dose button shelf 232 when the latter is in its distal actuated position.

Having described the different components of the trigger arrangement 200 as well as their functional relationship, the working principle for the trigger arrangement will be described with reference to the FIGS. 3A-3E.

Figure 3A:
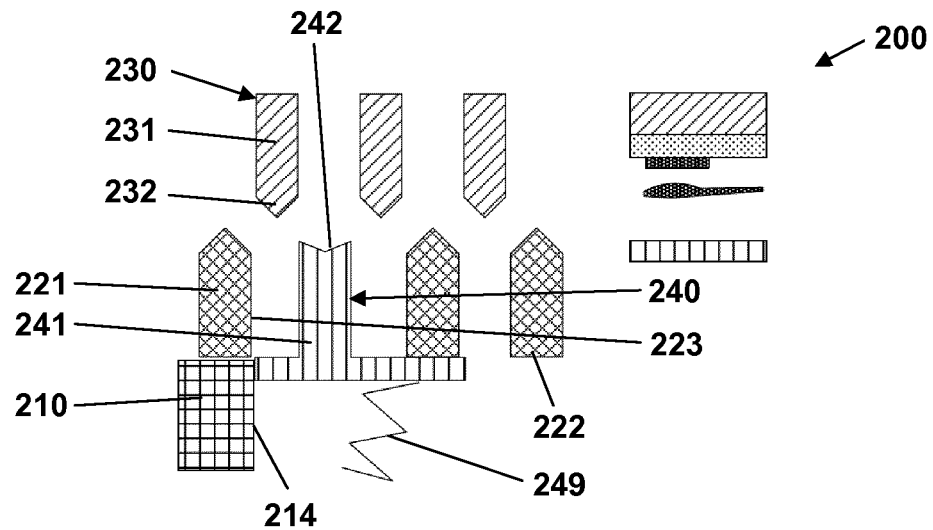
FIGS. 3A-3E show schematically a first embodiment of a trigger arrangement.

FIG. 3A shows the trigger arrangement 200 in an initial rest state with the dose button 230 in its proximal position, the scale drum member 210 in its initial end-of-dose position, and the trigger member 240 in its first trigger and first axial position. In this position the trigger spring 249 urges the trigger member into contact with the housing shelf 222 as well as the drum stop 214. The switch is open with the switch surface 246 positioned at a distance from the flexible switch arm.

Figure 3B:
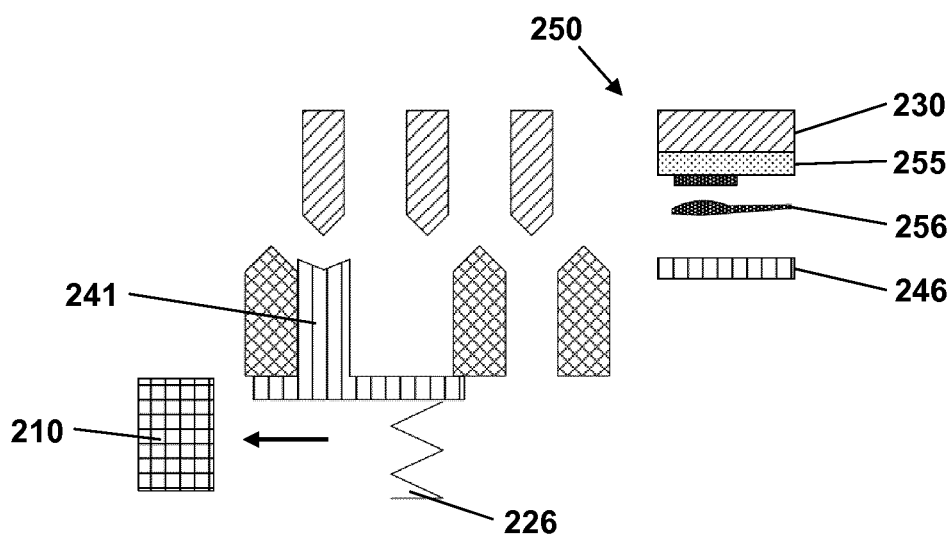

In FIG. 3B a dose has been set by rotating the dose button 230 whereby the scale drum member 210 has been rotated away from its initial end-of-dose position to a set position corresponding to the set dose amount. Correspondingly, the drum stop 214 has been moved out of engagement with the trigger member 240, this allowing the trigger spring 249 to move the trigger member from the first trigger position in contact with the drum stop 214 to the second trigger position in contact with the housing stop 223. As appears from FIG. 3B the trigger member is still supported axially by the housing shelf 222 in form of distally facing surfaces of the housing spline elements, this allowing the trigger member to be moved between the two positions without the risk of jamming. As also appears in FIG. 3B the trigger member locking structure 242 is moved into alignment with one of the dose button spline shelf surfaces 232. The number of dose button splines corresponds to the number of dose increments for one full rotation of the dose button, e.g. 24, such that the splines are shifted one position for each dose increment. In case the user decides to cancel the set dose by dialing back to zero, the scale drum member 210 will be moved back to the initial end-of-dose position and thereby also move the trigger member back to the first trigger position as shown in FIG. 3A.

Figure 3C:
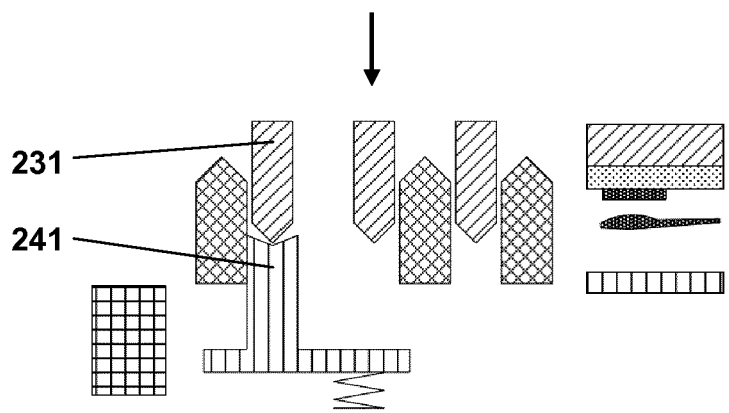

In FIG. 3C the dose button 230 has been moved to its distal position by a user to thereby start expelling a set dose. As the dose button is moved distally the button shelf surface 232 aligned with the trigger member engages the trigger member locking structure 242 and moves the latter distally, this compressing and thus energizing the trigger spring 249. The locking engagement 242, 232 between the trigger member and dose button shelf secures that the two structures do not rotate out of engagement with each other. As the dose button is actuated the spring driven expelling mechanism is released whereby the scale drum member starts to rotate back towards the initial end-of-dose position which in FIG. 3C has not yet been reached. Apart from a small initial gap between the button shelf surface 232 and the trigger member locking structure 242, the two members move axially together such that the EoD switch 250 stays open (for the switch components the movement corresponding to the closure of the initial gap is not shown in FIG. 3C). Correspondingly, if the user desires to pause the expelling of a set dose, the user can relieve the pressure on the dose button 230 which is then moved back to its proximal position by the button return spring (not shown) whereby the expelling mechanism including the scale drum member is "parked" corresponding to the remaining dose, this as shown in FIG. 3B. As appears, no activation of the switch takes place.

Figure 3D:
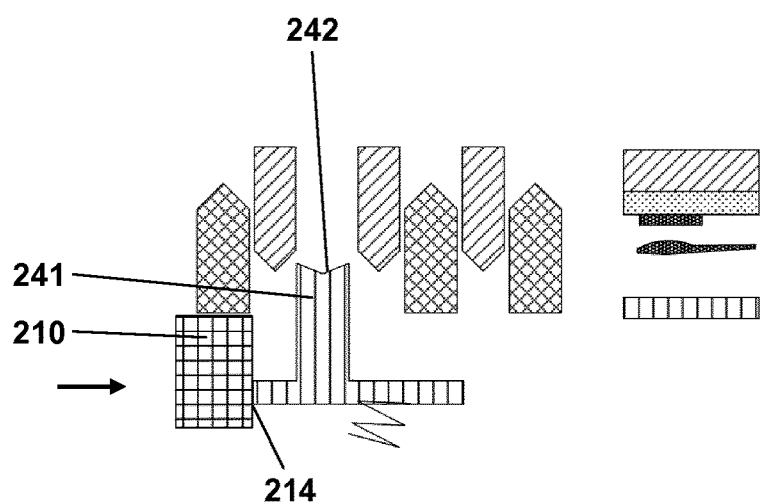
Figure 3E:
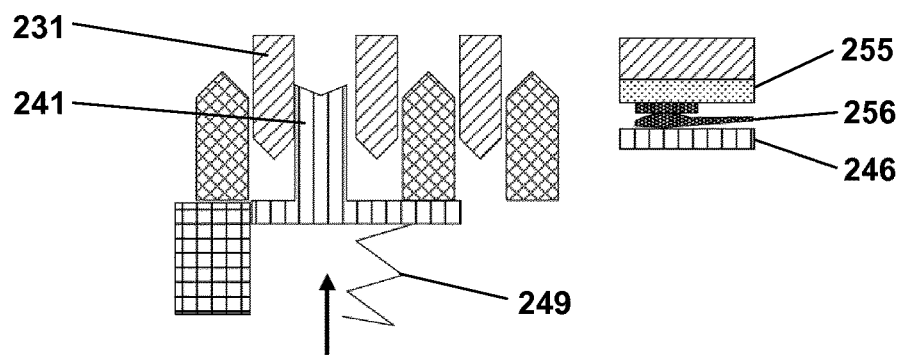

FIG. 3D shows the trigger arrangement 200 in an end-of-dose state with the dose button 230 still in its distal position, and the scale drum member 210 rotated back to its initial end-of-dose position. As the scale drum member reaches its rotational end-of-dose position it engages ("triggers") the trigger member 240 which is moved from its second to its first trigger position and thereby out of engagement with the button spline shelf 232, this allowing the trigger spring 249 to move the trigger member from its actuated second axial position in contact with a dose button shelf 232 to its first axial position in contact with the housing shelf 222. As the trigger member is moved proximally it engages the flexible switch arm 256 and thus triggers the EoD switch by closing the switch, this indicating to the associated electronic circuitry that an "EoD" state has been reached and a set dose has been fully expelled. After a given dose has been fully expelled, the user removes the pressure on the dose button 230 which subsequently is moved proximally by the return spring as shown in FIG. 3A, this re-opening the switch. However, if the dose expelling can be paused and the remaining dose thereafter is dialed back to zero, then no EoD state will be detected. Further, if the dose button is actuated and then released with the device in its initial state (see FIG. 3A) without a dose being set, then an EoD signal will be generated. To deal with this situation a mode switch may be provided which detects that the dose button is in its actuated distal position. Correspondingly, the electronic circuitry will be able to disregard an EoD signal if the dose button is not in its actuated distal position as detected by the mode switch. Alternatively, a rotary sensor may be used to detect that no dose has been set, this indicating that the dose button has been actuated with the device in its initial state. In any case, the detected EoD signal may be used to control e.g. a display incorporated in the device, see FIG. 5.

Next, with reference to schematic FIGS. 4A-4D a second embodiment (representing a second concept) of a trigger arrangement 300 for a drug delivery device of the spring-driven type will be described. Each of the figures schematically shows an indicator member in the form of a scale drum member 310, a housing part 320, an actuation member in the form of a combined dose setting and release member 330 ("dose button"), a trigger member 340, a trigger spring 349, a dose button return spring 339, and an End-of-Dose ("EoD") switch 350. A further actuation switch may be provided (not shown).

The housing part (which may be formed by one or more elements) comprises a trigger support portion 321 with an axial trigger member stop surface 322 (in the following also "housing shelf") and a second trigger member stop surface 323 (in the following also "housing stop"), an axial button stop surface 325, and a trigger spring support 326. The dose button 330 comprises an outer dose dial gripping surface 336, a proximal actuation surface 337, and an axial trigger member stop surface 335 (in the following also "button shelf"). The scale drum member 310 comprises a rotational trigger member stop surface 314 (in the following also "drum stop"). The EoD switch 350 is in the shown embodiment attached to the dose button and comprises a stationary portion (relative to the button) 355 and a movable portion in the form of a flexible arm 356, the two portions each comprising a contact point adapted to be arranged in an open respectively closed state. The trigger member 340 comprises a housing shelf engagement surface 342, a button shelf engagement surface 345, a housing stop engagement surface 343, a drum stop engagement surface 244, and a proximal switch surface 346 adapted to axially engage the flexible switch arm 356 to thereby close the switch. The trigger spring 349 is arranged between the trigger spring support 326 and the trigger member 340 and serves to provide (i) an inwards oriented biasing force to the trigger member (see below) and (ii) a distally directed biasing force ("trigger force"). The dose button return spring 339 is arranged between a support (e.g. the housing) and the dose button 330 and provides a proximally directed return force to the dose button.

The dose button is axially movable between an initial proximal position in which a user can rotate the button (or "dial") to set a dose amount of drug to be expelled, and an actuated distal position in which the expelling mechanism is released when a dose has been set. The scale drum member 310 is adapted to rotate helically corresponding to the general axis from an initial end-of-dose position in which no dose has been set to a set position corresponding to a set dose amount, and to rotate from the set position back to the end-of-dose position when the set dose has been expelled (or the mechanism has been dialed back to zero). The trigger member 340 is adapted to move between (i) a first trigger position in contact with the drum stop 314 when the latter is in the initial end-of-dose position, and (ii) a second trigger position in contact with the housing stop 323. The trigger member 340 is further adapted to move from (i) a first axial position in contact with the housing shelf 322, to (ii) a second axial position in contact with the dose button shelf 335 when the latter is in its distal actuated position.

Having described the different components of the trigger arrangement 300 as well as their functional relationship, the working principle for the trigger arrangement will be described with reference to the FIGS. 4A-4D.

Figure 4A:
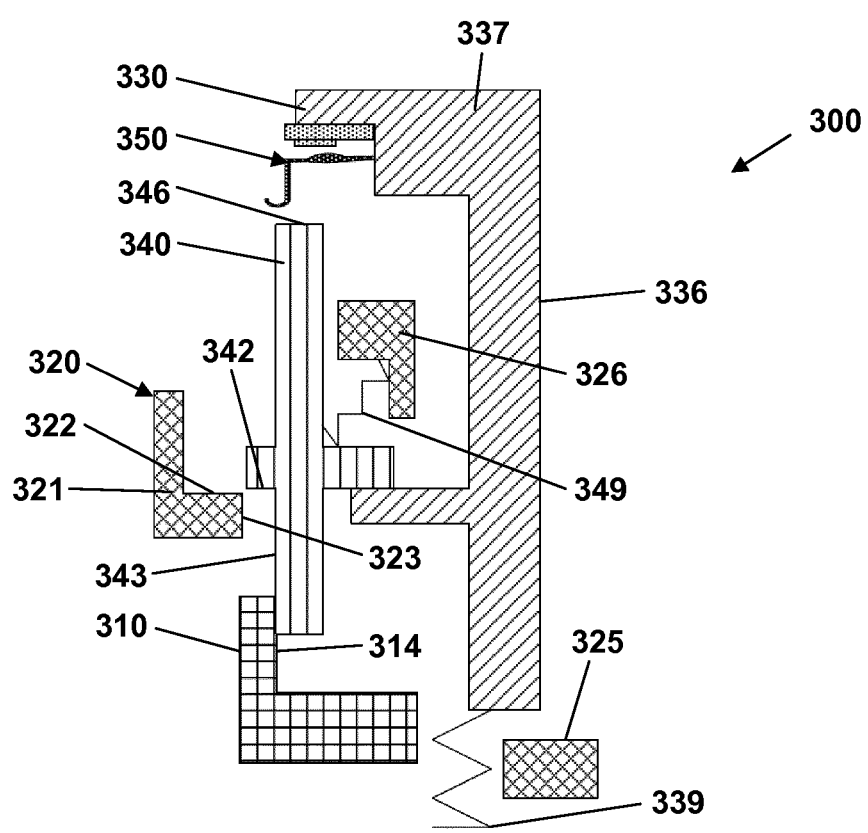
FIGS. 4A-4D show schematically a second embodiment of a trigger arrangement.

FIG. 4A shows the trigger arrangement 300 in an initial state with the dose button 330 in its proximal position, the scale drum member 310 in its initial end-of-dose position, and the trigger member 340 in its first trigger and first axial position. In this position the trigger spring 349 urges the trigger member into contact with the dose button shelf 335 as well as the drum stop.

Figure 4B:
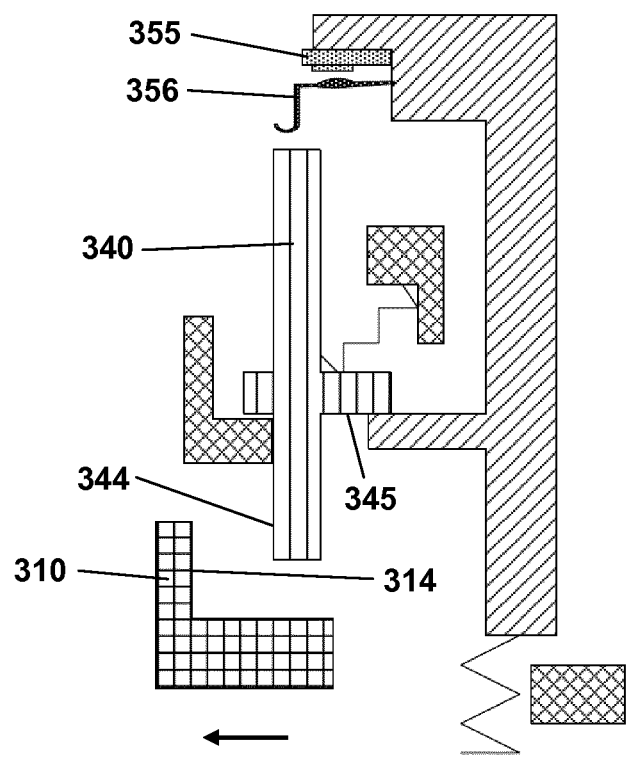

In FIG. 4B a dose has been set whereby the scale drum member 310 has been rotated away from its initial end-of-dose position to a set position corresponding to the set dose amount. Correspondingly, the drum stop 314 has been moved out of engagement with the trigger member 340, this allowing the trigger spring 349 to move the trigger member from the first trigger position in contact with the drum stop 314 to the second trigger position in contact with the housing stop 323. As appears from FIG. 4B the trigger member is still supported by the dose button shelf 335 but is positioned with a small gap to the housing shelf 322, this allowing the trigger member to be moved between the two positions without the risk of jamming. In case the user decides to cancel the set dose by dialing back to zero, the scale drum member 310 will be moved back to the initial end-of-dose position and thereby also move the trigger member back to the first trigger position as shown in FIG. 4A.

Figure 4C:
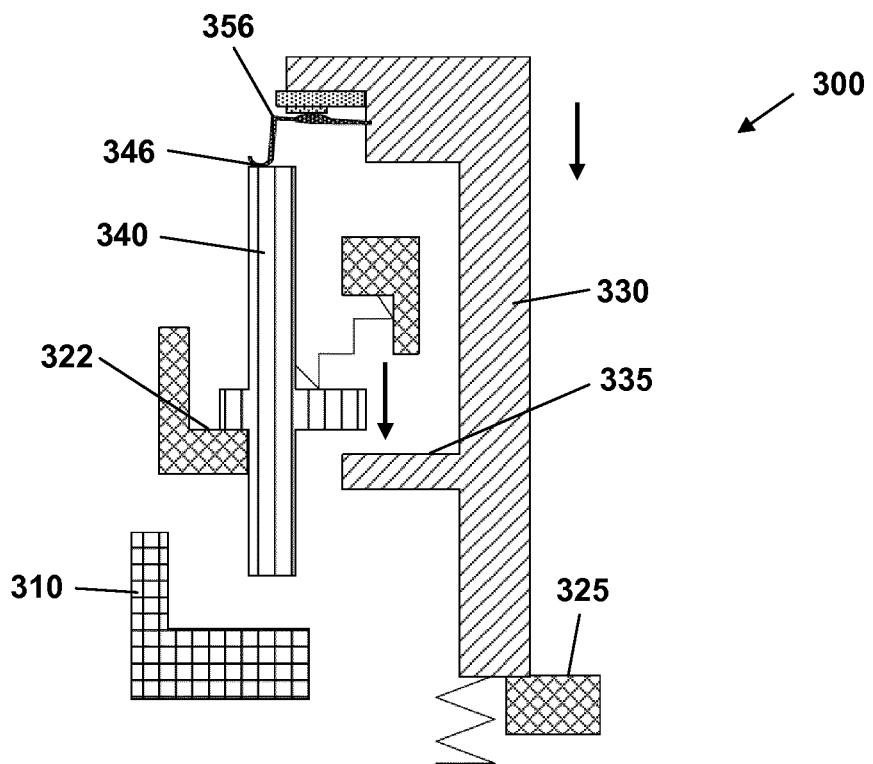

In FIG. 4C the dose button 330 has been moved to its distal position by a user to thereby start expelling a set dose. As the dose button is moved distally the flexible switch arm 356 engages the trigger member switch surface 346 thereby closing the EoD switch 350 which can then be detected by associated electronic circuitry. As the dose button is moved distally the dose button shelf 335 is moved out of engagement with the trigger member 340, this allowing the trigger spring to move the trigger member into axial engagement with the housing shelf 322. As the dose button is actuated the spring driven expelling mechanism is released whereby the scale drum member starts to rotate back towards initial end-of-dose position which in FIG. 4C has not yet been reached. Correspondingly, if the user desires to pause the expelling of a set dose, the user can relieve the pressure on the dose button 330 which is then moved back to its proximal position by the button return spring 339 whereby the expelling mechanism including the scale drum member is "parked" corresponding to the remaining dose. As the dose button is moved proximally the EoD switch is re-opened and the trigger member is moved slightly proximally to be again supported by the dose button shelf 335, this as shown in FIG. 4B.

Figure 4D:
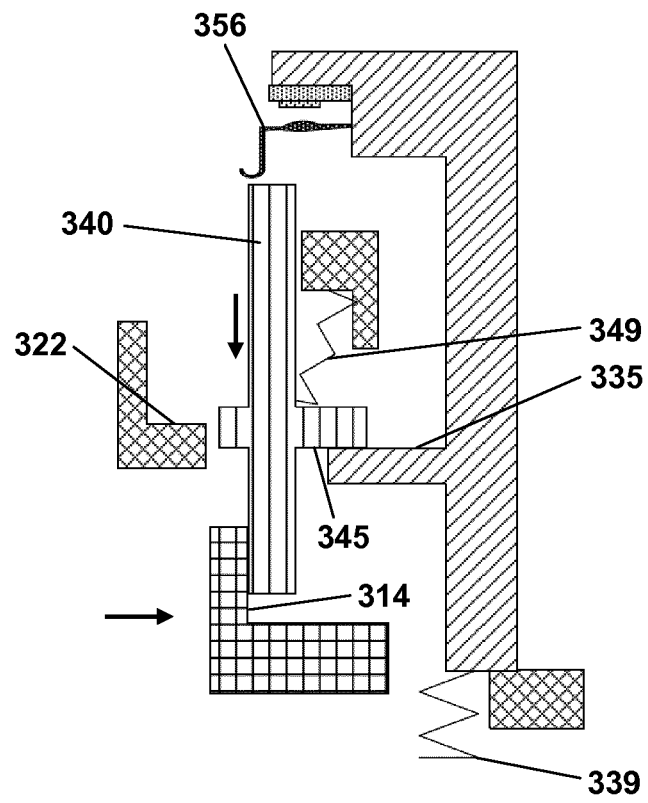

FIG. 4D shows the trigger arrangement 300 in an end-of-dose state with the dose button 330 still in its distal position, and the scale drum member 310 rotated back to its initial end-of-dose position. As the scale drum member reaches its rotational end-of-dose position it engages the trigger member 340 which is moved from its second to its first trigger position and thereby out of engagement with the housing shelf 322, however, as the dose button 330 at this state is positioned in its distal actuated position the dose button shelf 335 is correspondingly positioned in a distal position, this allowing the trigger spring 349 to move the trigger member from its first axial position in contact with the housing shelf 322 to its second axial position in contact with the dose button shelf 335 with the latter is in its distal actuated position. As the trigger member is moved distally it disengages the flexible switch arm 356 and thus triggers the EoD switch by re-opening the switch, this indicating to the associated electronic circuitry that an EoD state has been reached and a set dose fully expelled. After a given dose has been fully expelled, the user removes the pressure on the dose button 330 which subsequently is moved proximally by the return spring 339, whereby also the trigger member 340 is moved proximally by means of the dose button shelf 335, this causing the trigger spring to be energized (compressed) as shown in FIG. 4A.

However, as appears, the same signal was generated when an expelling action was paused as described above with reference to FIGS. 4C and 4B. In order to detect a "pause EoD" state and a "true EoD" state a second "mode" switch may be provided which detects the position of the dose button. Such a second switch could be arranged to detect whether or not the dose button is fully depressed, i.e. positioned in its actuated distal-most position. Correspondingly, with the dose button in its distal-most position the mode switch would be e.g. in a closed state, this indicating that opening of the EoD switch as in FIG. 4D would represent a "true EoD" event. On the other hand, if an expelling event is paused the mode switch would be adapted to open before the EoD switch is opened, this indicating a "pause EoD" to the associated electronics. If a paused dose is manually dialed back to zero the EoD switch would not be actuated.

As appears from the above description of two exemplary embodiments of the invention, they share the concept of comprising a trigger member arranged in an axially supported position against the action of the energized trigger spring, the trigger member being released from the axially supported position when an indicator member (here: scale drum) is rotated from a set position to an end-of-dose position, whereby the trigger member is moved axially by the trigger spring, this resulting in a switch being actuated.

In the first embodiment the trigger spring is energized when the dose button is actuated, however, the spring is only held in its energized state as long as the dose button is actuated. If the trigger member is actuated the spring will be released. Otherwise the spring will be de-energized as the dose bottom returns to its initial position. In contrast, in the second embodiment the trigger spring is energized when the dose button returns to its initial position driven by a dose button return spring, the trigger member being "parked" in an energized state resting on a housing shelf.

After having described first and second embodiments (or concepts) of a trigger arrangement using schematic figures, next a first embodiment of a pen-formed drug delivery incorporating the above-described first concept will be described with reference to FIGS. 5-8. The trigger arrangement is incorporated in a spring-driven pen-device comprising a dose logging module arranged in a combined dose setting and release button. The description will primarily focus on the incorporation of the trigger and to a lesser degree on the pen mechanism as such.

Figure 5:
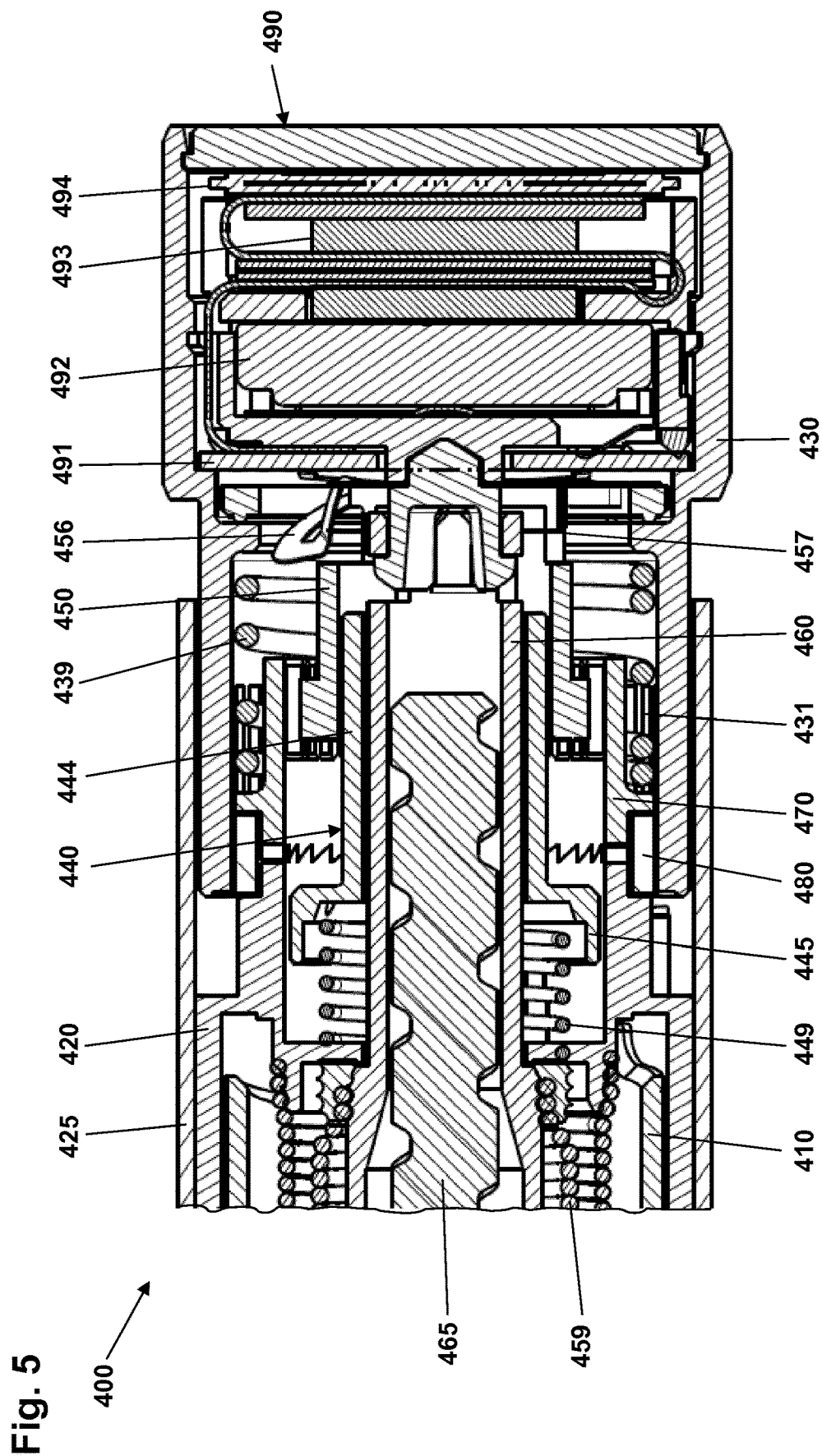
FIG. 5 shows in part a cross-sectional view of a drug delivery device.
Figure 6:
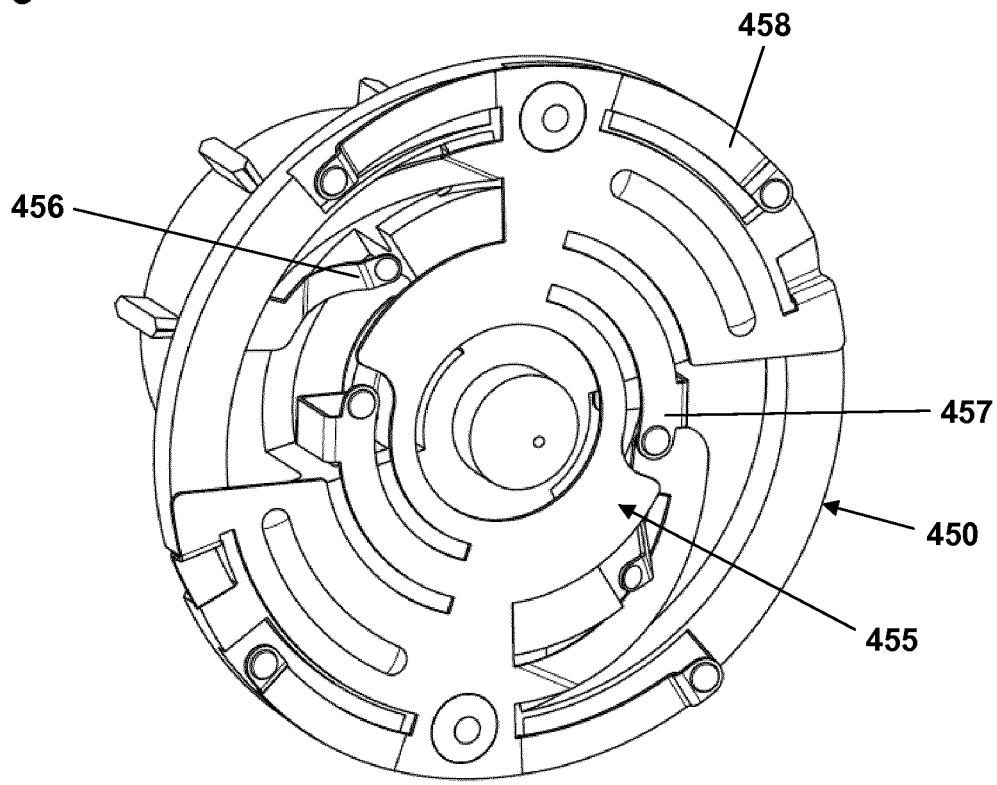
FIG. 6 shows a switch disc incorporated in the device of FIG. 5.

FIG. 5 shows the proximal portion of a drug delivery device 400 in a dose setting state, the device comprising an inner housing member 420 in which a scale drum 410 is helically guided, a protective outer housing member 425, a piston rod 465, a drive tube 460, a double-wound helical torsion drive spring 459 arranged between the housing and the drive tube, a transmission member 450, a ratchet member 470, a ratchet release member ("lifter") 480, a combined dose setting and release member (dose button) 430, a dose button return spring 439, a trigger member 440, and a trigger spring 449.

In the interior of the dose button a logging module 490 is arranged, the module comprising a distally facing contact disc 491, an electric cell 492, electronic circuitry 493, a display 494 and a transparent window 495, all components being non-rotationally arranged in the dose button. A proximally-facing switch disc 455 is non-rotationally attached to the transmission member 450 (see FIG. 6), the disc comprising a pair of long-travel mode switch arms 456, a pair of EoD switch arms 457, and a number of encoder switch arms 458 adapted to cooperate with corresponding contact structures on the contact disc 491, the latter two structures together forming a rotary sensor.

The transmission member 450 is mounted axially and rotationally locked to the drive tube 460 and in releasable splined engagement with the ratchet member 470, which is in splined rotationally locked engagement with a circumferential array of dose button splines 431. A uni-directional ratchet interface is provided between the ratchet member 470 and the housing member 420, however, the ratchet release member 480 provides that the ratchet member can be lifted out of engagement with the housing whereby a set dose can be reduced incrementally. The latter arrangement is described in greater detail in EP 15156962.1.

The trigger member 440 comprises a proximal tubular portion 444 arranged around the drive tube 460, as well as a distal skirt portion 445 in engagement with the trigger spring 449. The skirt portion is provided with a pair of opposed control portions 447 (not to be seen in FIG. 5, see FIG. 7) received in corresponding cut-outs in the housing member, this allowing the trigger member to move axially and rotate slightly as will be described in greater detail below. Each control portion is essentially identical and each provided with a pair of trigger splines 441 (see FIG. 7), however, in this embodiment only one of the trigger portions is arranged to engage the scale drum member 410.

In the shown embodiment the ratchet release member 480 serves as a proximal stop for the trigger member, i.e. it serves as the "housing shelf". The ratchet release member 480 may be coupled to the housing member 420 to allow rotation there between but prevent axial movement there between. Alternatively, the ratchet release member 480 may be held in place by the ratchet member 470 urging the ratchet release member in the distal direction towards the housing member. In the latter case this would result in the ratchet release member and the trigger element 440 moving slightly back and forth during dose setting due to the proximally directed force from the trigger spring 449.

The drive spring 459 is coupled between the housing and the drive tube at its ends, the dose button return spring 439 is supported between the dose button 430 and the ratchet member 470, the trigger spring 449 is supported between the housing member 420 and the trigger member 440, and the scale drum is rotationally coupled to the drive tube at the distal end (not shown).

Figure 7:
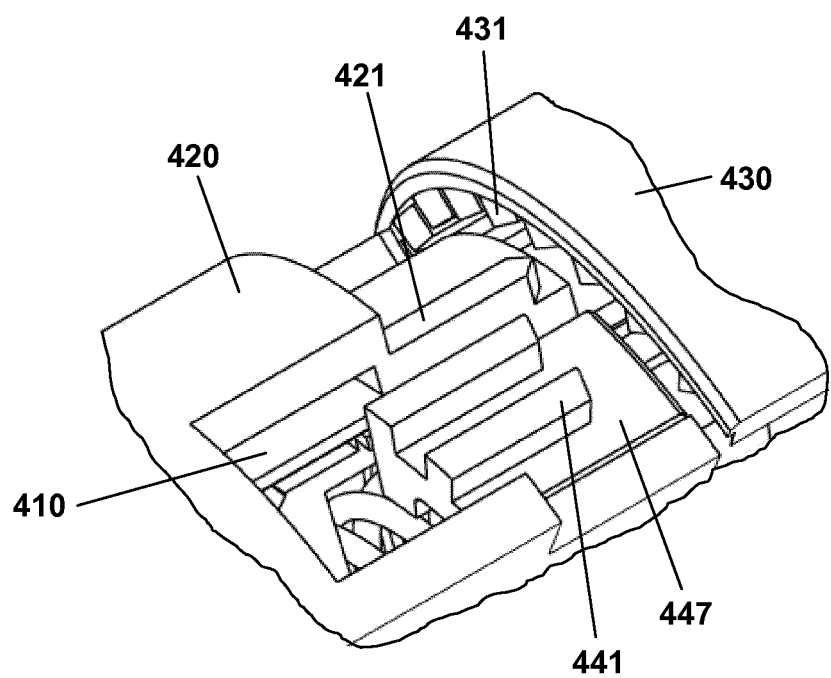
FIG. 7 shows components of the trigger arrangement incorporated in the device of FIG. 5, FIGS. 8A-8D show actuation of the trigger member incorporated in the device of FIG. 5.

FIG. 7 shows the housing member 420, the dose button 430, a trigger member control portion 447 and the scale drum 410 in an initial state with the scale drum in its zero position in engagement with the trigger member. The figure also shows the housing splines 421, the dose button splines 431 and the trigger member splines 441. To allow the scale drum to be seen a portion of the housing member has been cut away.

When setting a dose the dose button 430 is rotated clock-wise whereby the thereto coupled ratchet member 470, transmission member 450, drive tube 460 and the scale drum rotate therewith, this straining the drive spring 459. Due to the ratchet interface between the ratchet member and the housing member 420 the rotated components are held in the set position. As will be described in greater detail below, the trigger member is rotated slightly clockwise. As the dose button 430 and the transmission member 450 rotate together no relative rotational movement is detected by the rotary sensor.

When a dose has been set and the dose button 430 is actuated, the dose button, the transmission member 450 and the drive spring is moved distally. During the initial axial movement the dose button splines 431 engage an outer array of housing splines 421 (see FIG. 7) whereby the dose button is rotationally locked to the housing. At the same time the mode switch arms 456 engage the proximal end of the ratchet member to thereby switch the mode switch in its actuated (closed) mode. At the distal end of the expelling mechanism (not shown) a drive clutch provides that the drive tube 460 is rotationally coupled to a piston rod driver. When the dose button is moved further distally the trigger member is actuated and the trigger spring compressed, the transmission member 450 disengages the ratchet member, this allowing the strained spring to rotate the drive tube 460 counter-clock-wise, whereby the piston rod driver causes the piston rod 465 to rotate and move distally to expel drug. As the transmission member 450 rotates with the drive tube the rotary sensor detects rotational movement corresponding to the dose amount being expelled. At the same time the scale drum 410 is rotated helically back towards its initial zero position. When the scale drum at the zero position engages the trigger member 440 the latter is released and moved proximally by the trigger spring 449, the trigger member proximal surface 446 thereby actuating (closing) the EoD switch, this indicating to the logging circuitry that a set dose has been fully expelled, the dose size corresponding to the detected rotational movement between the transmission member and the dose button.

When pressure on the dose button is released the return spring 439 returns the dose button to its initial proximal position, whereby the EoD switch re-opens, the transmission member 450 re-engages the ratchet member 470, the drive clutch disengages, the mode switch re-opens and the dose button disengages the housing member.

With reference to FIGS. 8A-8E the actuation of the trigger member 440 will be described in greater detail. FIGS. 8A-8E show the embodiment of FIG. 5 without the outer housing 425, however, to better allow the scale drum 410, the dose button splines 431 and the trigger member control portion 447 to be seen, the outer circumferential distal portion of the dose button as well as a portion of the housing member have been cut away.

Figure 8A:
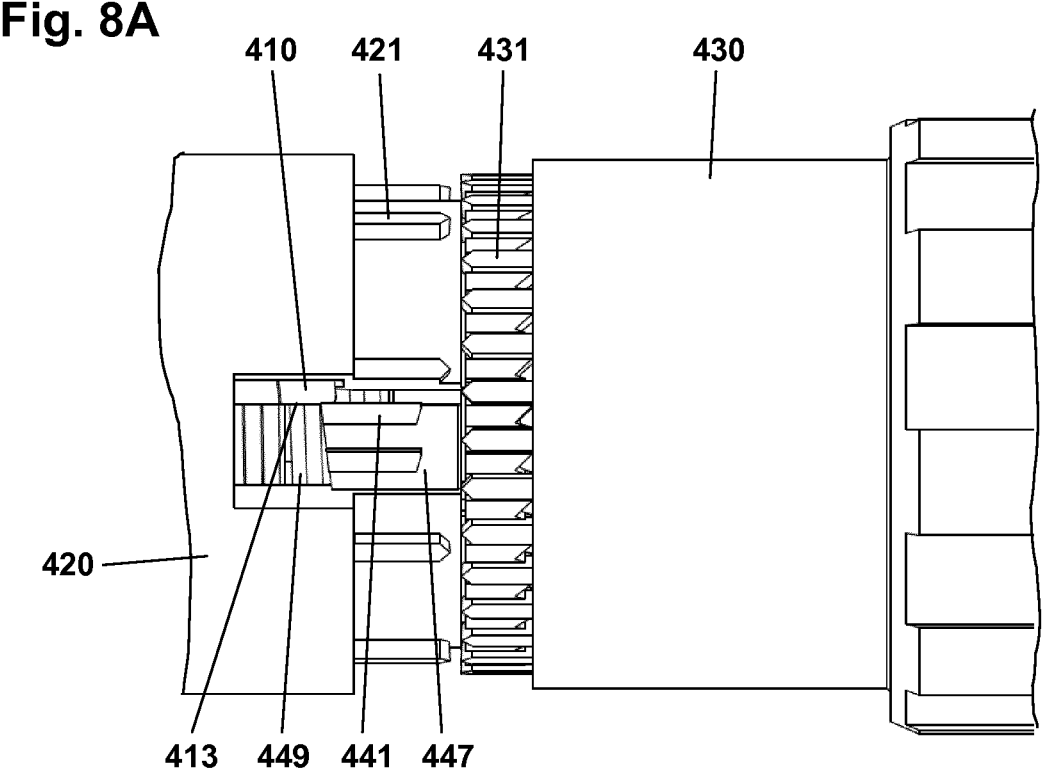

FIG. 8A shows the trigger arrangement of the drug delivery pen 400 in an initial rest state with the dose button 430 in its proximal position, the scale drum member 410 in its initial end-of-dose position, and one of the trigger member control portions 447 in its rotational and axial initial position. In this position the trigger spring 449 urges the trigger member into its proximal-most position as well as into contact with the scale drum stop edge 214.

Figure 8B:
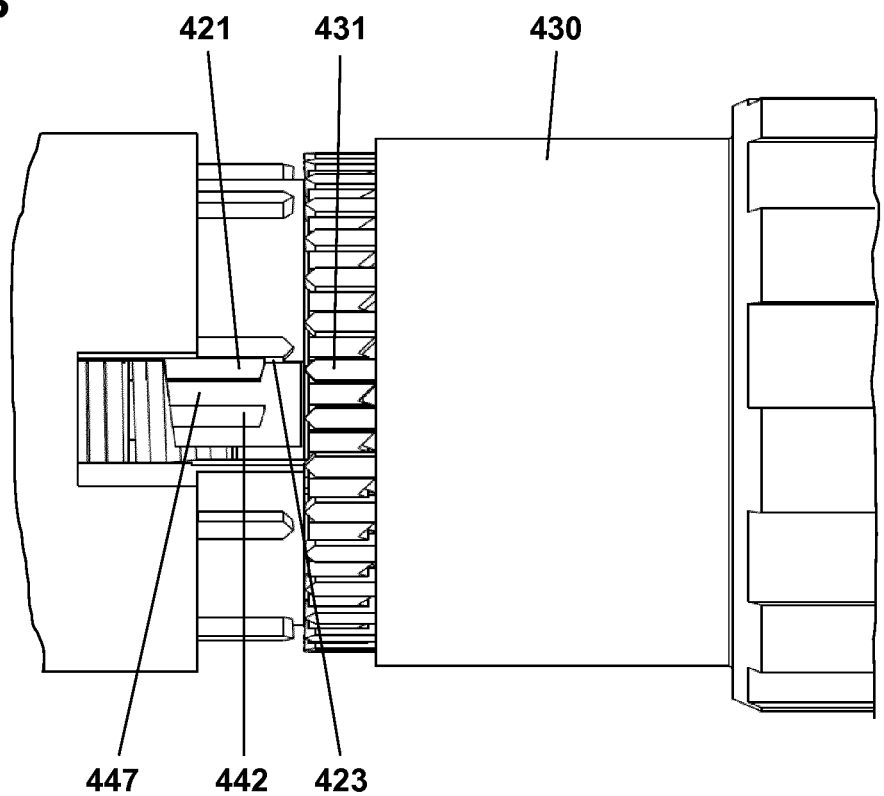

In FIG. 8B a dose has been set by rotating the dose button 430 whereby the scale drum member 410 has been rotated away from its initial end-of-dose position to a set position corresponding to the set dose amount. Correspondingly, the scale drum stop has been moved out of engagement with the trigger member control portion 447, this allowing the trigger spring 449 to move the trigger member into contact with the housing stop surface 423. As also appears in FIG. 8B the two trigger member splines 441 are moved into alignment with a pair of dose button splines 431.

Figure 8C:
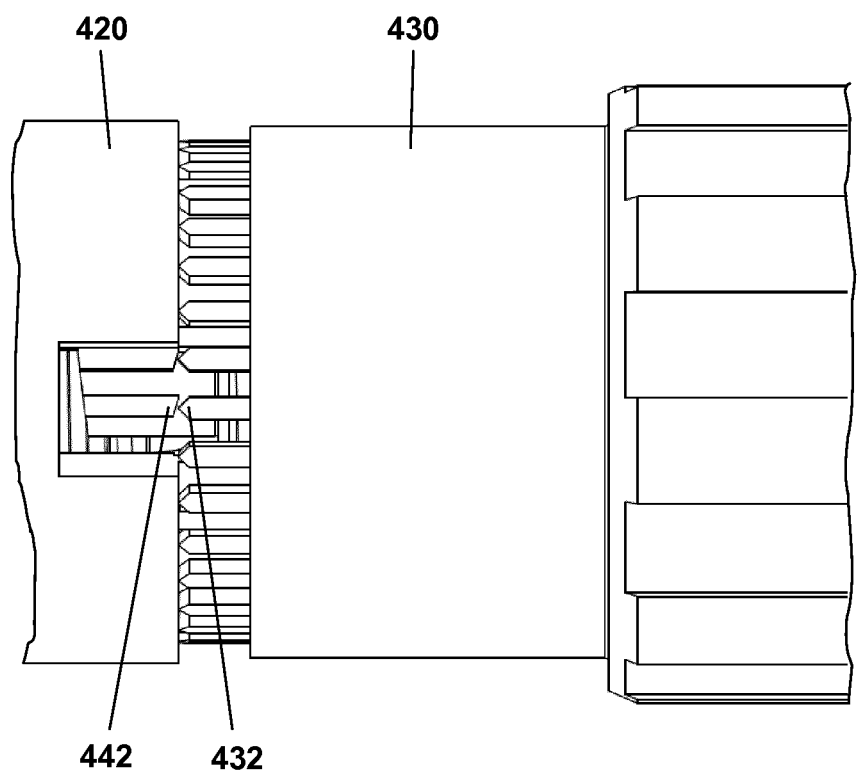

In FIG. 8C the dose button 430 has been moved to its distal position to thereby start expelling a set dose. As the dose button is moved distally the dose button splines 431 engage housing splines 421 whereby the dose button is rotationally locked to the housing 420. The dose button splines 431 aligned with the trigger member splines 421 engage the proximal end thereof and moves the latter distally, this compressing and thus energizing the trigger spring 449. The chamfered design of the engaging spline ends 432, 442 ensures that the trigger member does not rotate relative to the dose button. As the dose button 430 is actuated the spring driven expelling mechanism is released whereby the scale drum member starts to rotate back towards the initial end-of-dose position which in FIG. 8C has not yet been reached.

Figure 8D:
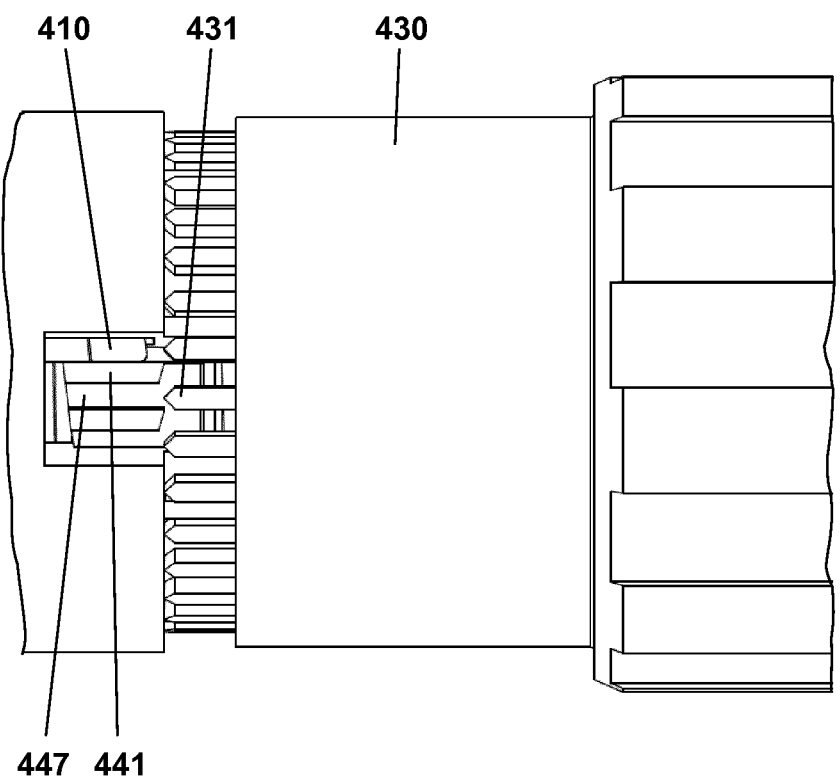
Figure 8E:
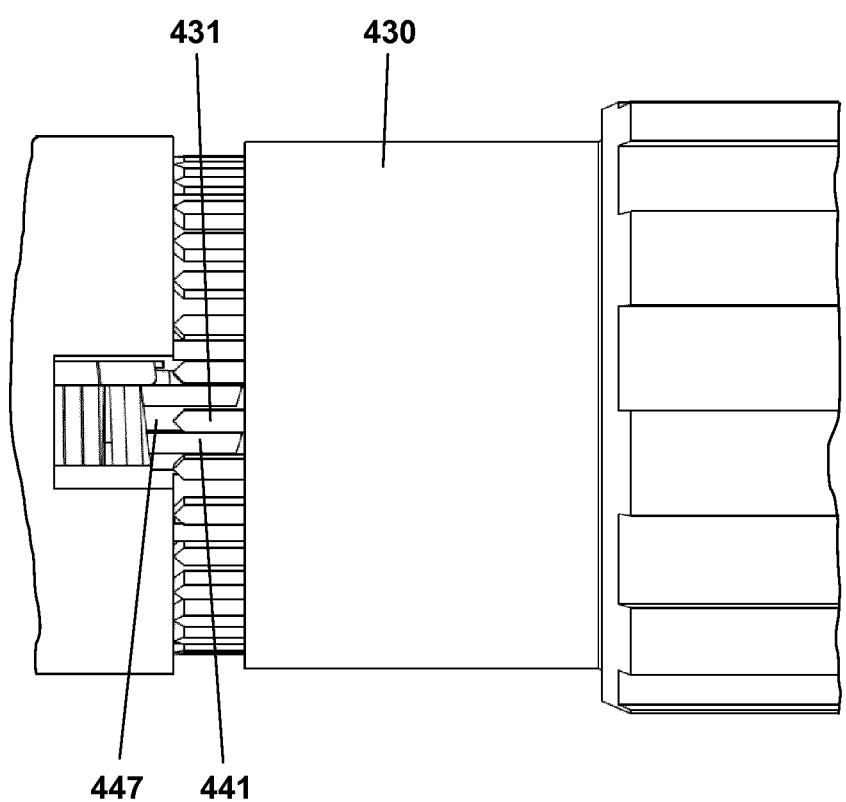

FIG. 8D shows the trigger arrangement in an end-of-dose state with the dose button 430 still in its distal position, and the scale drum member 410 rotated back to its initial end-of-dose position. As the scale drum member reaches its rotational end-of-dose position it engages the trigger member control portion 447 which is moved to its initial rotational position and thereby out of engagement with the button splines 431, this allowing the trigger spring 449 to move the trigger member axially from its actuated distal position to its released proximal position, the trigger member splines 441 sliding between the dose button splines 431 as shown in FIG. 8E. As the trigger member is moved proximally it engages the flexible switch arm 456 and thus triggers the EoD switch by closing the switch, this indicating to the associated electronic circuitry that an "EoD" state has been reached and a set dose has been fully expelled. After a given dose has been fully expelled, the user removes the pressure on the dose button 430 which subsequently is moved proximally by the return spring to the position shown in FIG. 8A, this re-opening the switch and results in an audible and/or tactile signal to the user.

Next a second embodiment of a pen-formed drug delivery incorporating the above-described second concept will be described. The trigger arrangement is incorporated in a spring-driven pen-device comprising a dose logging module arranged in a combined dose setting and release button. The description will primarily focus on the incorporation of the trigger and to a lesser degree on the pen mechanism as such.

Figure 9:
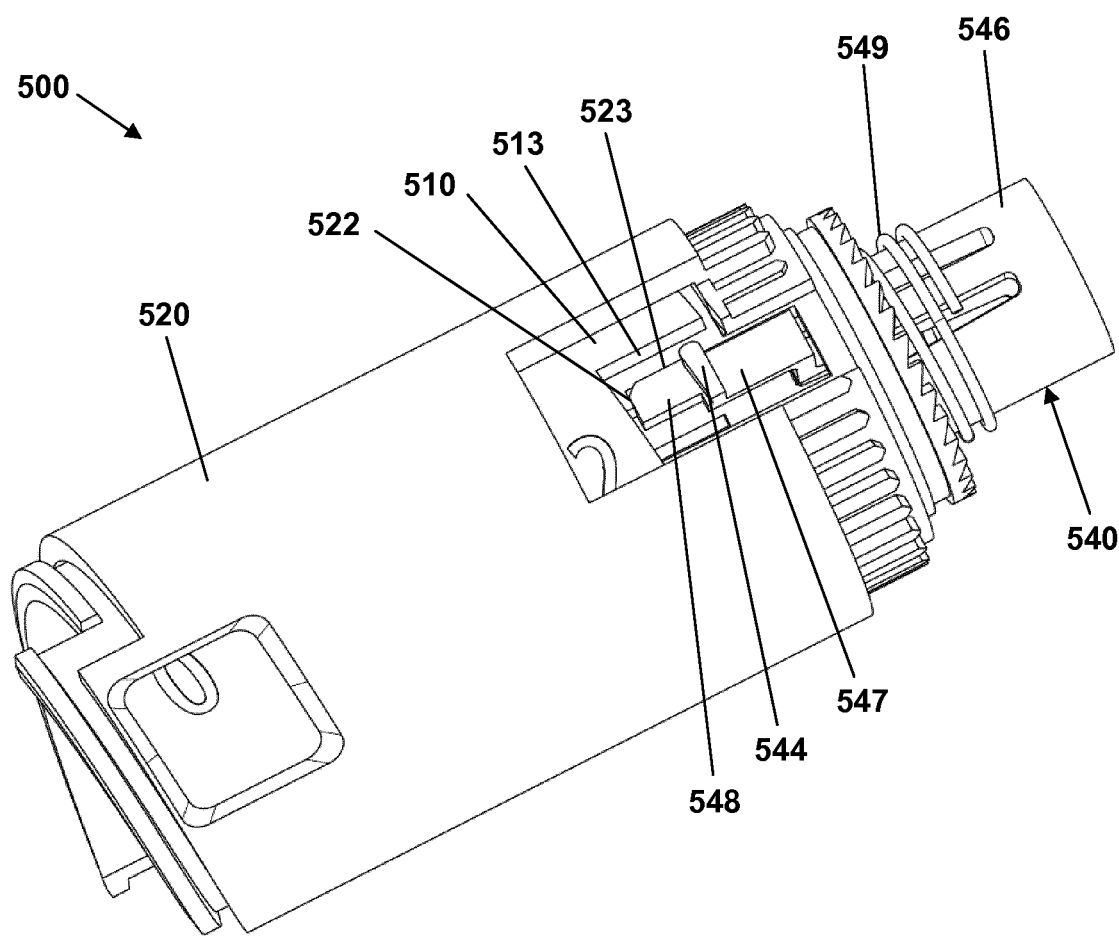
FIG. 9 shows components of a trigger arrangement corresponding to FIGS. 4A-4D incorporated in a drug delivery device.

FIG. 9 shows the proximal portion of a partly assembled drug delivery device 500 in a dose setting state, the device comprising a housing member 520 (which for illustrative purposes is cut open to reveal the functional portion of the trigger member) in which a scale drum 510 is helically guided, a trigger member 540, and a trigger spring 549.

Corresponding to the above-described embodiment of FIG. 5 the drug delivery device 500 also comprises a number of not shown components: a piston rod, a drive tube, a torsion drive spring, a ratchet member, a ratchet release member, a dose button, a dose button return spring, and a switch disc. In the dose button a logging module is arranged, the module comprising a distally facing contact disc adapted to cooperate with corresponding contact structures on the switch disc, the latter two structures together forming a rotary sensor.

In respect of the dose setting and expelling mechanism per se, the drug delivery device 500 functions similarly to the device of FIG. 5. Correspondingly, only the specific implementation of the trigger member 540 will in the following be described in greater detail.

Referring first to FIG. 4A the trigger member 340 comprises a housing shelf engagement surface 342, a button shelf engagement surface 345, a housing stop engagement surface 343, a drum stop engagement surface 344, and a proximal switch surface 346 adapted to axially engage the flexible switch arm 356 to thereby close the switch. In the embodiment of FIG. 9 the trigger member has been redesigned and the above-described engagement surfaces have been rearranged.

The trigger member 540 comprises a proximal ring portion 546 which is arranged axially movable but non-rotationally relative to the housing, and a distally extending trigger arm 547 which due to its flexibility can move slightly sideways.

The housing member 520 comprises an inner wall portion with a cut-out providing both a "housing stop" 523 and a "housing shelf" 522. In contrast to the schematic embodiment of FIG. 4A the "button shelf" has been transferred to the drive tube coupled to the dose button and moving axially therewith, thus providing the same functionality. In its initial zero position the proximal portion of the scale drum 510 with the "drum stop 513" is arranged to helically rotate in the circumferential space between the housing member outer and inner wall.

Corresponding to above-described shelf and stop surfaces the trigger arm 547 comprises a distal-most end portion adapted to engage the housing shelf and the housing stop. As the scale drum is arranged circumferentially outside the housing cut-out the trigger member is provided with a radial "trigger" protrusion 544 adapted to engage the drum stop. The trigger member further comprises an inner engagement surface (not seen) adapted to engage the "button shelf" (which as indicated above is not arranged on the dose button in the FIG. 9 embodiment).

In FIG. 9 the pen device is in a dosing state corresponding to FIG. 4C in which the trigger member is supported against the housing stop 523 and the housing shelf 522 with the scale drum approaching the trigger 544. When the scale drum reaches its zero position the trigger arm is moved out of engagement with the housing shelf and thereby allowed to be moved to its distal position by the trigger spring 549.

The trigger arrangements described with reference to FIGS. 5-9 are incorporated in spring-driven pen devices provided with a dose logging assembly comprising first and second rotary sensor parts adapted to rotate relative to each other during operations of the device, wherein the electronic circuitry is adapted to calculate dose amounts based on relative rotation between the first and second rotary sensor parts. In the specific embodiments described the sensor parts are adapted to rotate relative to each other during dose expelling.

The rotary sensor could be designed to provide rotational input to the electronic circuitry in different ways. For example, the rotary sensor may generate a signal for each incremental rotation between the sensor parts, e.g. one increment corresponding to a rotation of 15 degrees which for a given insulin formulation may correspond to one unit of insulin. The signals could then be counted until the end-of-dose signal is generated, this indicating that a set dose has been fully expelled. After the end-of-dose signal is detected the counted value can be stored in a memory and the counter reset. As the rotary sensor parts only rotates relative to each other during expelling, an expelling event can be paused and the remaining dose adjusted, this having no influence on the detected amount of rotation.

In an alternative design the rotary decoder is designed to detect a given position, the calculated dose amount being based on a detected start-of-dose rotational position and a detected end-of-dose rotational position. For dose sizes corresponding to more than one full rotation a rotation-counter would have to be provided. To detect the start-of-dose rotational position a mode switch may be provided.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device, comprising:
 a drug-filled cartridge or structure for receiving a drug-filled cartridge, the cartridge comprising an outlet and an axially displaceable piston,
 drug expelling structure comprising:
   dose setting structure allowing a user to set a dose amount of drug to be expelled,
   a piston rod adapted to engage and axially move the piston to thereby expel an amount of drug from the cartridge through the outlet,
   an indicator member adapted to rotate corresponding to a reference axis from an initial end-of-dose position to a set position corresponding to a set dose amount, and to rotate from the set position back to the end-of-dose position when the set dose has been expelled,
   a trigger member,
   an actuation member for causing the piston rod to expel the set dose amount, the actuation member being moveable between an initial position and an actuated position,
   a trigger spring acting on the trigger member, the trigger spring being energized by movement of the actuation member,
   the trigger member is rotated from a first trigger position to a second trigger position when the indicator member is rotated from the initial end-of-dose position to a set position, and is rotated from the second trigger position back to the first trigger position when the indicator member is rotated from a set position to the end-of-dose position,
   with the trigger member in the second trigger position, the actuation member is adapted to engage and thereby move the trigger member axially from the initial to the actuated position when the actuation member is moved from the initial position to the actuated position, whereby the trigger spring is energized, and
 a sensor system comprising:
   electronic circuitry adapted to:
     generate and store data related to an expelled dose amount, and detect when an end-of-dose switch is actuated,
the actuation member and the trigger member comprise cooperating locking structure preventing non-axial movement there between when engaged,
wherein the trigger member is adapted to be:
arranged in an axially supported biased position against the action of the energized trigger spring, and
released from the axially supported biased position by the indicator member, directly or indirectly, when the indicator member is rotated from a set position to the end-of-dose position thereby releasing the locking structure whereby the trigger member is rotated from the second to the first position, this allowing the trigger member to move from the actuated position back to the initial position,
wherein the end-of-dose switch adapted to be actuated, directly or indirectly, by axial movement of the trigger member, and
whereby the trigger member is moved axially by the trigger spring, the end-of-dose switch thereby being actuated providing an end-of-dose input to the electronic circuitry.

2. A drug delivery device as in claim 1, wherein:
the trigger spring is energized when the actuation member is moved from the actuated position to the initial position with the trigger member in the second trigger position.

3. A drug delivery device as in claim 1, wherein:
the trigger member axially engages a support when the actuation member is moved from the initial position to the actuated position with the trigger member in the second trigger position.

4. A drug delivery device as in claim 3, wherein:
the trigger member is released from the support and rotated from the second to the first position when the indicator member is rotated from a set position to the end-of-dose position, this allowing the trigger member to be moved axially by the trigger spring.

5. A drug delivery device as in claim 1, further comprising:
a biasing structure for biasing the trigger member towards the second position.

6. A drug delivery device as in claim 5, wherein the biasing structure is provided by the trigger spring.

7. A drug delivery device as in claim 1, wherein:
the drug expelling structure further comprises a drive spring,
the dose setting structure is adapted to simultaneously set the dose amount to be expelled and strain the drive spring correspondingly, and
the actuation structure is adapted to release the drive spring to thereby move the piston rod in the distal direction corresponding to the set dose.

8. A drug delivery device as in claim 1, further comprising:
first and second rotary sensor parts adapted to rotate relative to each other during dose setting and/or dose expelling,
wherein the electronic circuitry is adapted to calculate dose amounts based on relative rotation between the first and second rotary sensor parts during setting and/or expelling of a dose of drug.

9. A drug delivery device as in claim 8, wherein a dose amount is calculated when the electronic circuitry receives an input from the end-of-dose switch.

10. A drug delivery device as in claim 8, wherein the electronic circuitry comprises logging structure adapted to create a log for calculated dose amounts of drug.

11. A drug delivery device as in claim 1, further comprising a mode switch arranged to provide an input to the electronic circuitry when the actuation member is in its actuated position.

12. A drug delivery device comprising:
a drug-filled cartridge or structure for receiving a drug-filled cartridge, the cartridge comprising an outlet and an axially displaceable piston,
drug expelling structure comprising:
dose setting structure allowing a user to set a dose amount of drug to be expelled,
a piston rod adapted to engage and axially move the piston to thereby expel an amount of drug from the cartridge through the outlet,
an indicator member adapted to rotate corresponding to a reference axis from an initial end-of-dose position to a set position corresponding to a set dose amount, and to rotate from the set position back to the end-of-dose position when the set dose has been expelled,
a trigger member,
an actuation member for causing the piston rod to expel the set dose amount, the actuation member being moveable between an initial position and an actuated position,
a trigger spring acting on the trigger member, the trigger spring being energized by movement of the actuation member,
the trigger member is moved from a first trigger position to a second trigger position when the indicator member is rotated from the initial end-of-dose position to a set position, and is moved from the second trigger position back to the first trigger position when the indicator member is rotated from a set position to the end-of-dose position,
the trigger spring is energized when the actuation member is moved from the actuated position to the initial position with the trigger member in the second trigger position,
the trigger member axially engages a support when the actuation member is moved from the initial position to the actuated position with the trigger member in the second trigger position,
when the actuation member is actuated with the trigger member in the second trigger position, then the trigger member is moved back to the first trigger position when the indicator member is rotated from a set position to the end-of-dose position, whereby the trigger member is moved axially by the trigger spring,
a sensor system comprising:
electronic circuitry adapted to:
generate and store data related to an expelled dose amount, and
detect when an end-of-dose switch is actuated,
wherein the trigger member is adapted to be:
arranged in an axially supported biased position against the action of the energized trigger spring, and
moved from the second to the first position when the indicator member is rotated from a set position to the end-of-dose position, and thereby released from the support and thus the axially supported biased position, this allowing the trigger member to be moved axially by the trigger spring,
wherein the end-of-dose switch adapted to be actuated, directly or indirectly, by axial movement of the trigger member, and whereby the trigger member is moved axially by the trigger spring, the end-of-dose switch thereby being actuated providing an end-of-dose input to the electronic circuitry.

13. A drug delivery device as in claim 12, wherein:
  with the trigger member in the second trigger position, the trigger member is moved axially from an initial position to an actuated position when the actuation member is moved from the initial position to the actuated position, whereby the trigger spring is energized.

14. A drug delivery device as in claim 12, wherein the locking structure is released and the trigger member is rotated from the second to the first position when the indicator member is rotated from a set position to the end-of-dose position, this allowing the trigger member to move from the actuated position back to the initial position.

* * * * *

UNITED STATES PATENT AND TRADEMARK OFFICE
CERTIFICATE OF CORRECTION

| | |
|---|---|
| PATENT NO. | : 11,197,957 B2 |
| APPLICATION NO. | : 15/738393 |
| DATED | : December 14, 2021 |
| INVENTOR(S) | : Kiilerich et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this
Thirty-first Day of January, 2023

*Katherine Kelly Vidal*

Katherine Kelly Vidal
*Director of the United States Patent and Trademark Office*